(12) United States Patent
DeWoolfson et al.

(10) Patent No.: US 12,295,882 B1
(45) Date of Patent: May 13, 2025

(54) BAFFLE DEVICES AND RELATED METHODS FOR DELIVERY OF THERAPEUTIC COMPOSITIONS TO THE EYE (71) Applicant: D&D Biopharmaceuticals, LLC, Sterling, VA (US)

(72) Inventors: Bruce H. DeWoolfson, Sterling, VA (US); Michael Luttrell, Dayton, OH (US); Dale P. DeVore, Chelmsford, MA (US)

(73) Assignee: D&D Biopharmaceuticals, LLC, Sterling, VA (US)

( * ) Notice: Subject to any disclaimer, the term of this patent is extended or adjusted under 35 U.S.C. 154(b) by 0 days.

(21) Appl. No.: 18/887,672

(22) Filed: Sep. 17, 2024

(51) Int. Cl.
*A61F 9/00* (2006.01)

(52) U.S. Cl.
CPC .................. *A61F 9/0008* (2013.01)

(58) Field of Classification Search
CPC ..... A61F 9/0026; A61F 9/0008; A61F 9/0017
See application file for complete search history.

(56) References Cited

U.S. PATENT DOCUMENTS

| | | | |
|---|---|---|---|
| 8,306,613 B2 | 11/2012 | Roy | |
| 8,480,638 B2 | 7/2013 | Tuitupou et al. | |
| 9,399,102 B2 | 7/2016 | DeWoolfson et al. | |
| 10,206,814 B2 | 2/2019 | Hardten et al. | |
| 10,342,697 B2 | 7/2019 | Friedman et al. | |
| 11,259,959 B1* | 3/2022 | DeWoolfson | A61F 9/0026 |
| 11,938,092 B1 | 3/2024 | DeWoolfson et al. | |
| 2011/0086802 A1 | 4/2011 | DeWoolfson et al. | |
| 2016/0067083 A1* | 3/2016 | Lue | A61F 9/0017 606/107 |
| 2021/0030591 A1 | 2/2021 | El-Ayari | |
| 2024/0189188 A1 | 6/2024 | DeWoolfson et al. | |

FOREIGN PATENT DOCUMENTS

| | | |
|---|---|---|
| WO | 2022/098633 A1 | 5/2022 |
| WO | 2024/118773 A1 | 6/2024 |

OTHER PUBLICATIONS

Kim, H.M. et al., "Ocular Drug Delivery to the Retina: Current Innovations and Future Perspectives," Pharmaceutics, vol. 13, No. 108, pp. 1-32 (2021).

* cited by examiner

*Primary Examiner* — Susan S Su
*Assistant Examiner* — Erin A Kim
(74) *Attorney, Agent, or Firm* — Bookoff McAndrews, PLLC (57) ABSTRACT

Medical devices, e.g., baffle devices, and related methods of use to administer therapeutic compositions to the eye are described. The medical device may include a body defining a lumen and including an intermediate portion that includes a compressible bellows. The device may have a flared distal end configured to contact a convex surface of the eye.

20 Claims, 5 Drawing Sheets

BAFFLE DEVICES AND RELATED METHODS FOR DELIVERY OF THERAPEUTIC COMPOSITIONS TO THE EYE

TECHNICAL FIELD

The present disclosure is directed to devices for topical delivery of active agents to an eye of a subject, e.g., in preparation for, during, and/or after a medical procedure.

BACKGROUND

The treatment of many ophthalmic diseases and post-operative conditions require frequent administration of drugs to the ocular tissues. Many medications must be applied topically to the eye, and one common form of treatment is the use of drops or ointments. The topical formulation is administered by the patient or caregiver using an eyedropper or dispenser. For ophthalmic therapeutics that are dispensed from an eyedropper or squeeze bottle, as much as 90% or more runs off the eye and is often wasted, or cannot remain on the eye for a sufficient time to achieve its intended therapeutic effect. Further, a substantial disadvantage of eyedroppers and dispensers is that the medication can rapidly drain from the ocular surface into the lacrimal system through an opening in the eyelid called the punctum. Other therapeutics are embedded in gels or ointments in order to keep the therapeutic agent in contact with the surface tissues for longer periods but these gels and ointments interfere with normal vision and dissolve or dissipate from the eye in an uneven and uncontrolled manner. Furthermore, the medications can be rapidly diluted by tears secreted by the lacrimal gland, and preservatives in multi-dose bottles can cause irritation or more serious complications to ocular tissues. Another approach for localized drug delivery involves the injection of the drug directly under the conjunctiva or Tenon capsule, intracamerally or intra-vitreally. This approach can require periodic injections of the drug to maintain an effective concentration at the target site and has many potential adverse effects. Current treatment methods like these can result in sporadic delivery of medication with unpredictable dosage at the target tissue. Intermittent administration can also lead to an initial overdosage with a rapid decrease in concentration to ineffective levels, due to dilution and lacrimal drainage.

SUMMARY

The present disclosure includes medical devices and related methods of treatment. For example, an exemplary medical device of the present disclosure comprises a body defining a lumen and including an intermediate portion that includes a compressible bellows; wherein the device has a flared distal end configured to contact a convex surface of an eye. According to some aspects, the device further comprises a handle, e.g., a handle component, configured to be gripped by a user, the handle being integral with or coupled to the body. The device may comprise a biocompatible polymer. In some examples, a wall thickness of the bellows ranges from about 0.01 cm to about 0.1 cm. Additionally or alternatively, an inner angle of the bellows may range from about 45 degrees to about 75 degrees. In some examples, a maximum width of the device is defined by the bellows, the distal end, or both the bellows and the distal end. The bellows may be closer to the distal end than to a proximal end of the device opposite the distal end.

The present disclosure also includes a method of treating an eye of a subject, the method comprising placing a distal end of a medical device against a surface of the eye, wherein the device includes a body defining a lumen, the body comprising an intermediate portion that includes a compressible bellows, and wherein the distal end of the device forms a seal against the surface of the eye; and introducing a therapeutic composition to the lumen to contact the surface of the eye. The distal end of the device may flare radially outward. In some aspects, placing the distal end of the device against the surface of the eye includes compressing a portion of the bellows while a remainder of the bellows is uncompressed or expanded. For example, an inner angle of the bellows in a neutral position may range from about 45 degrees to about 75 degrees, wherein the portion of the bellows is compressed relative to the neutral position. A wall thickness of the bellows may range from about 0.01 cm to about 0.1 cm. The therapeutic composition may comprise one or more active agents and a buffer solution. In some examples, the composition contacts the surface of the eye for about 30 seconds to about two minutes. The subject being treatment may have, for example, keratoconus or astigmatism. Optionally, the device may be centered on a cornea of the eye when the composition contacts the surface of the eye. In some examples, the device is off-center relative to a cornea of the eye when the composition contacts the surface of the eye.

In further aspects, the present disclosure includes a medical device comprising a body defining a lumen and including an intermediate portion that includes a compressible bellows, wherein a wall thickness of the bellows ranges from about 0.01 cm to about 0.1 cm and an inner angle of the bellows ranges from about 45 degrees to about 75 degrees; wherein the device has a flared distal end configured to contact a convex surface of an eye. The bellows may be closer to the distal end than to a proximal end of the device opposite the distal end. In some aspects, a length of the device from a proximal end to the distal end ranges from about 1 cm to about 5.5 cm.

It is to be understood that both the foregoing general description and the following detailed description are exemplary and explanatory only and are not restrictive of the present disclosure, as claimed.

BRIEF DESCRIPTION OF THE DRAWINGS

The accompanying drawings, which are incorporated in and constitute a part of this application, illustrate various exemplary embodiments and together with the description, serve to explain the principles of the disclosed embodiments.

DETAILED DESCRIPTION

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value. Any aspect described herein as exemplary is not to be construed as preferred or advantageous over other aspects. Rather, the term "exemplary" is used in the sense of example or illustrative.

The medical devices herein may provide effective and controlled topical delivery of a therapeutic composition, e.g., an ophthalmic composition, to the eye. The composition may be in liquid form, e.g., formulated as a solution or a low viscosity gel. For example, the composition may comprise one or more active agents and a buffer solution. The devices herein may be baffle devices configured to direct the composition to the surface of the eye and maintain the composition in contact with the eye for a desired period of time. For example, the composition may remain in contact with the surface of the eye for at least 30 seconds, e.g., one minute or two minutes, for effective delivery of a desired dose of the active agent(s) to target tissues of the eye, without significant run off of the composition during administration. The baffle devices herein may be sufficiently flexible to bridge over different portions of the eye, such as portions of the epithelium, the limbus, and the sclera during a single application. For example, the baffle devices may include a bellows able to adapt the devices to different eye shapes and sizes.

A significant challenge in topical delivery of medication to the eye is accommodating the convex curvature of the eye, and particularly variations in eye shape among different subjects. The cornea of the eye bulges slightly in a rounded dome shape. However, this shape can be more conical (e.g., for subjects with keratoconus) or irregular (e.g., for subjects with astigmatism) among different subjects, which further complicates administration of therapeutics. The medical devices herein may provide for bespoke delivery of therapeutic ophthalmic compositions through features able to accommodate different eye shapes. In particular, the devices of the present disclosure are configured as a baffle with a bellows that may compress or expand to adapt to different eye shapes. The devices also include a flared end to gently rest against the surface of the eye and form a seal able to retain liquid and gel medications within the device and in contact with the eye. The medical devices herein may comprise silicone, rubber, plastic, or other biocompatible polymers (e.g., polyethylene, polypropylene, polyurethane, polyvinyl chloride, etc.).

Figure 2A:
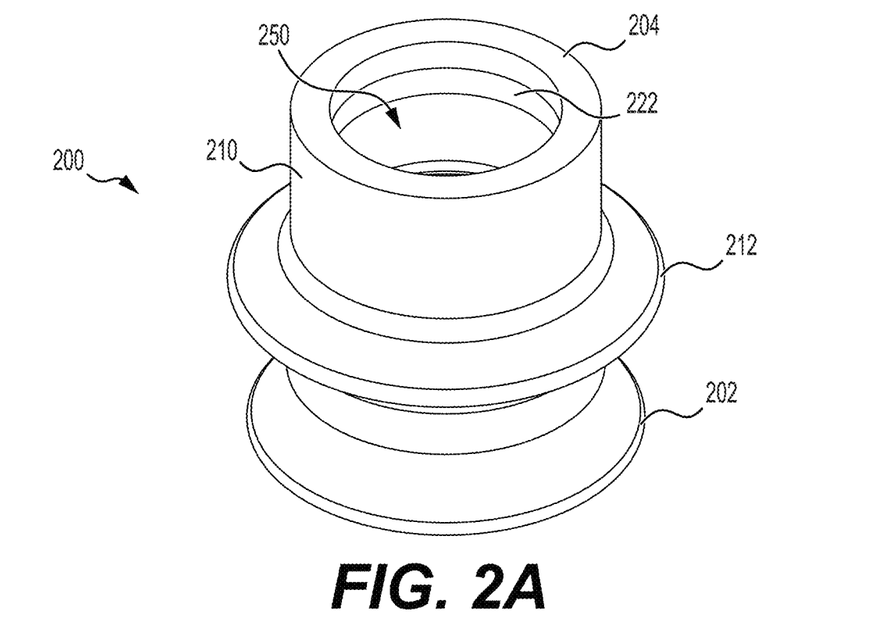
FIGS. 2A-2B show an exemplary medical device, according to some aspects of the present disclosure.
Figure 2B:
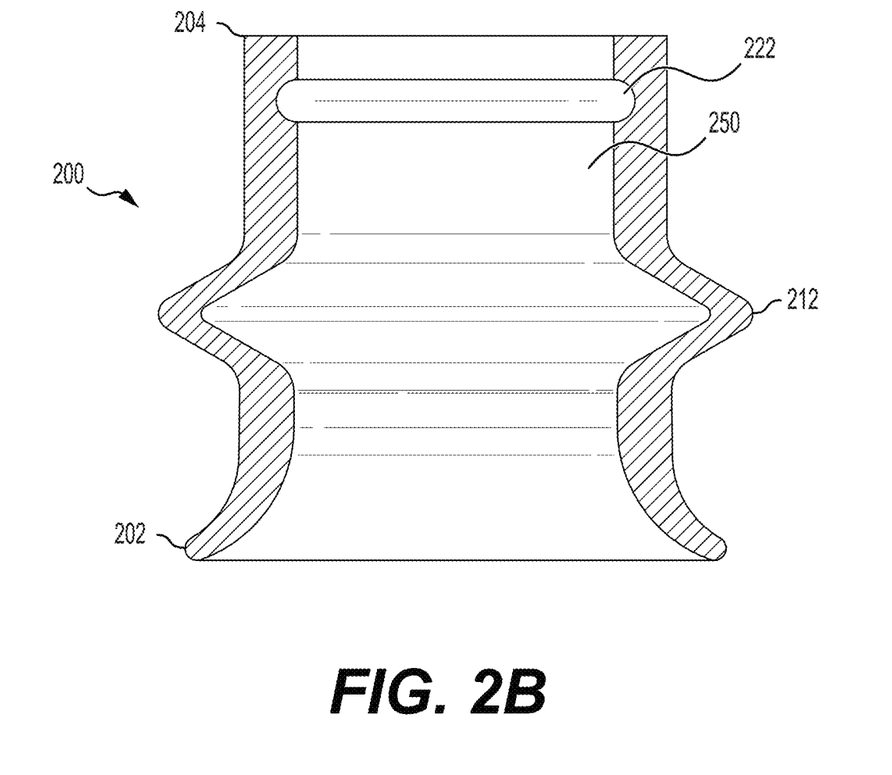
Figure 3:
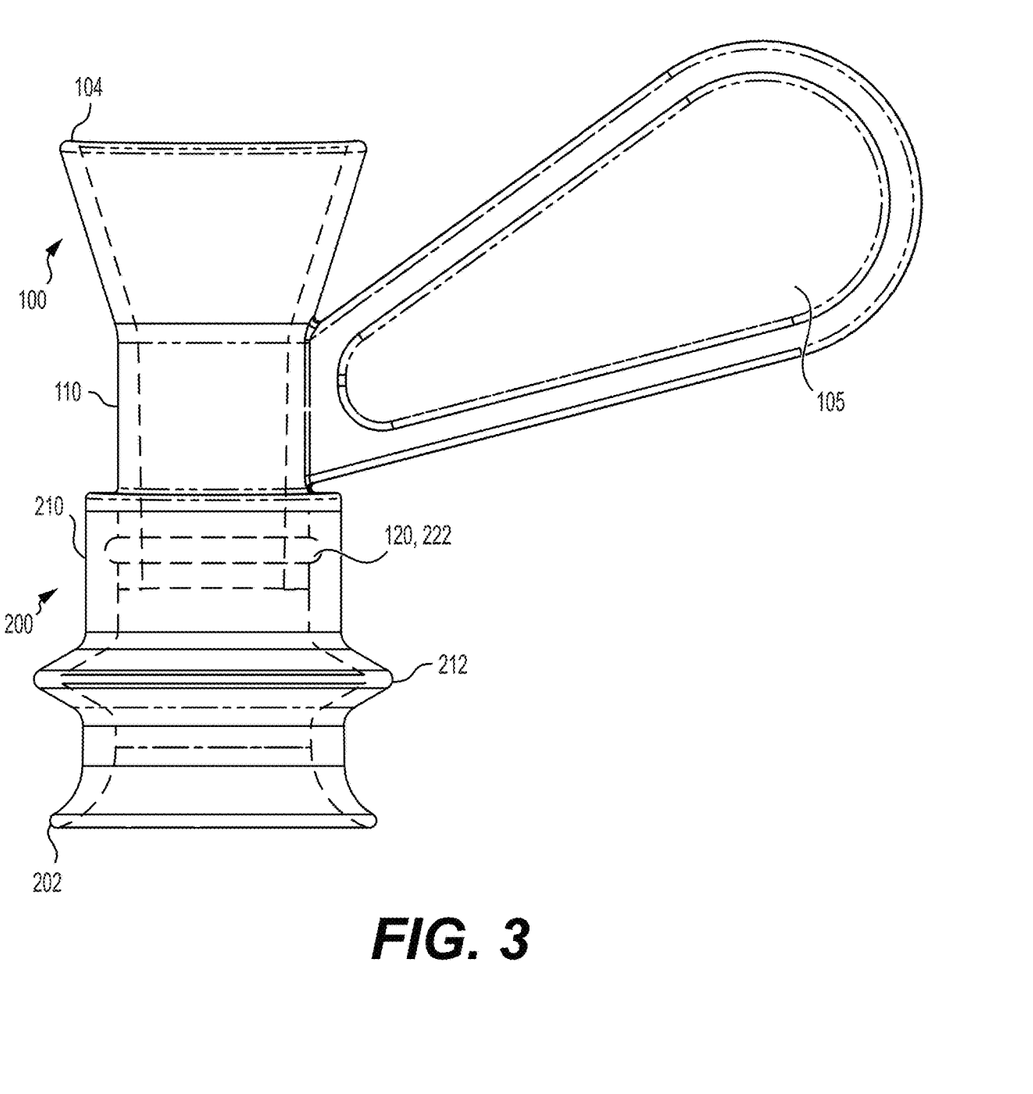
FIG. 3 shows the medical device of FIGS. 2A-2B and the handle component of FIGS. 1A-1B coupled together.
Figure 4:
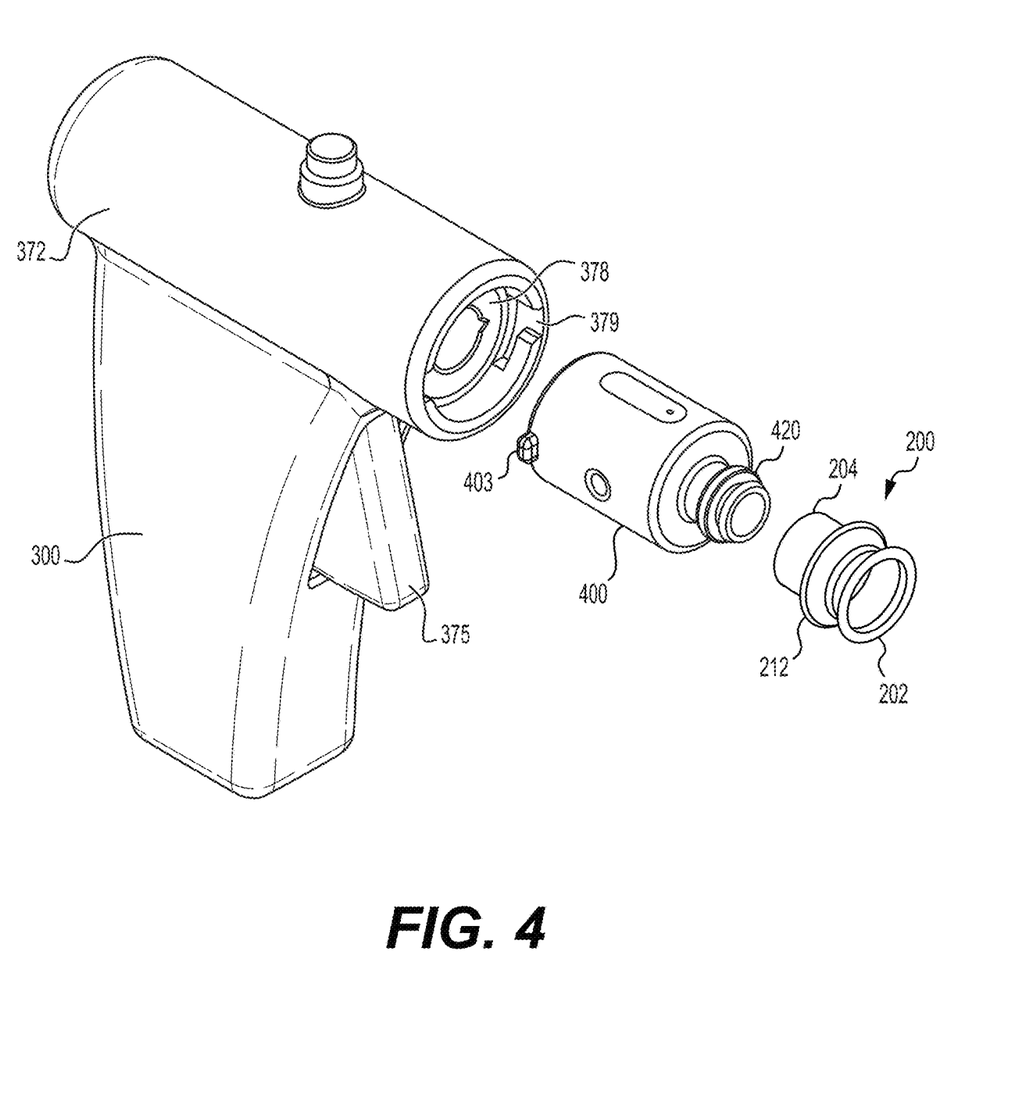
FIG. 4 shows an exemplary delivery device and cartridge with the medical device of FIGS. 2A-2B, according to some aspects of the present disclosure.

Medical devices according to the present disclosure optionally may be used in conjunction with a handle component or a delivery device. For example, FIGS. 2A and 2B illustrate an exemplary medical device 200, alternatively referred to as a baffle device. The medical device 200 may be coupled to a handle component 100 shown in FIGS. 1A-1B as illustrated in FIG. 3; or may be used in conjunction with a delivery device 300 as illustrated in FIG. 4. Further, in some cases, the medical device 200 may be used to administer a composition without a handle or a delivery device.

Figure 1A:
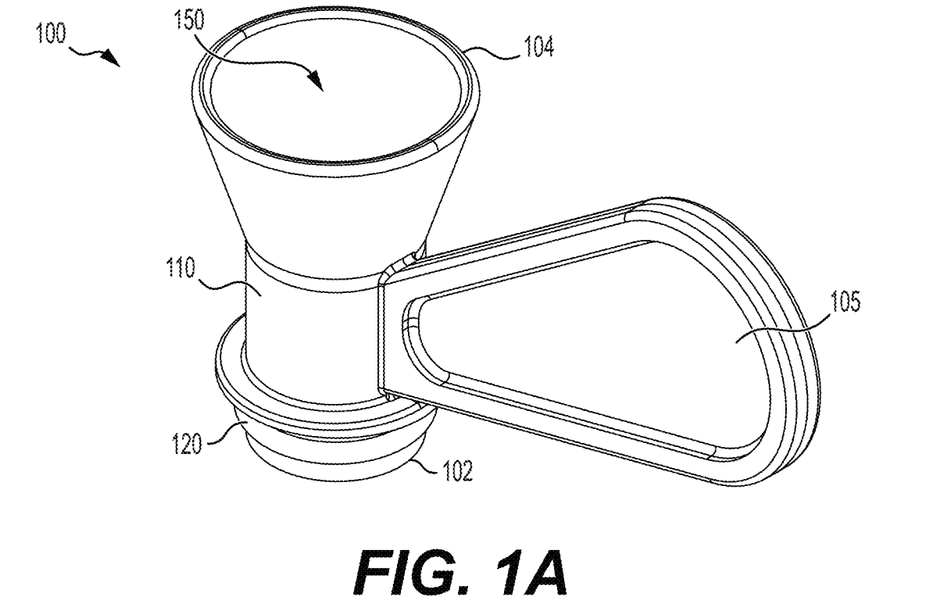
FIGS. 1A-1B show an exemplary handle component for a medical device, according to some aspects of the present disclosure.
Figure 1B:
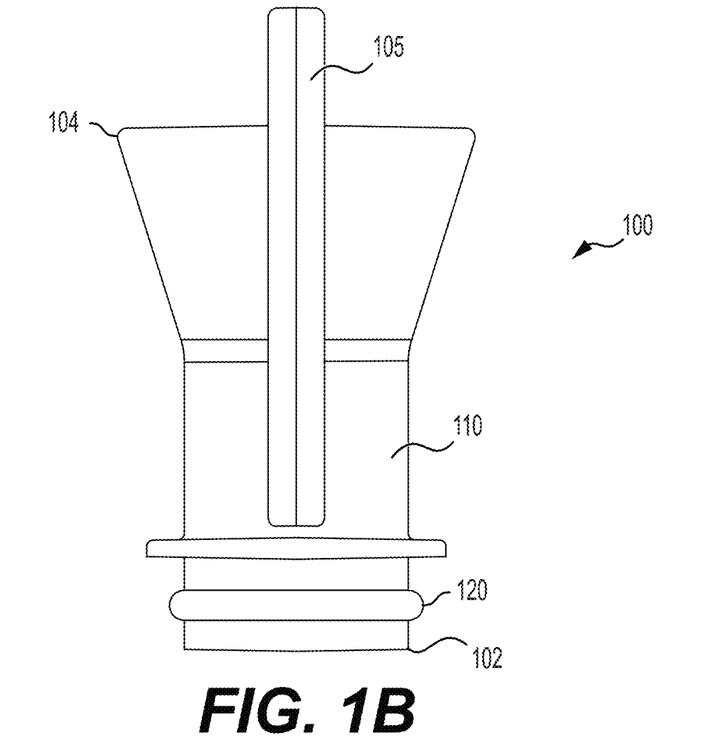

Referring to FIGS. 1A and 1B, the handle component 100 comprises a body 110 that extends from a proximal end 104 to a distal end 102. The body 110 may be generally cylindrical and define a lumen with open proximal and distal ends for receiving and delivering a therapeutic composition to the eye. In some examples, the proximal end 104 may taper as shown to provide a flared end to facilitate receiving a therapeutic composition. In other examples, the proximal end 104 does not taper and has a generally cylindrical shape, similar to the shape of the body 110. Handle component 100 includes a handle 105 configured to be gripped and held by the hand of a user (physician or other medical professional). The handle 105 may be integral with the body 110, fixedly attached to the body 110, or attachable and detachable from the body 110, e.g., via complementary engagement elements such as clips, magnets, tongue/groove, etc. The handle 105 may facilitate maintaining the handle component 100 in contact with the eye during administration of a therapeutic composition. At least a portion of the handle component 100 may be flexible. In some aspects, substantially all of the handle component 100 is flexible. Optionally, the handle 105 may be relatively more rigid than the body 110 such that a user can grip the handle 105 during treatment of a subject.

The material and wall thickness of the body 110 of the handle component 100 may be selected to be compatible with the material and flexibility of the medical device 200 (discussed below), which sufficient durability for ease of use in a medical procedure. In some aspects, the wall thickness of the body 110 may be less than 0.1 cm, e.g., ranging from about 0.01 cm to 0.1 cm, or from about 0.04 cm to about 0.09 cm. The total length of the handle component 100 from proximal end 104 to distal end 102 may range from about 1 cm to about 3 cm, such as about 1.5 cm to about 2.5 cm. The cross-sectional dimension (e.g., diameter) of the lumen 150 of the body 110 may range from about 0.2 cm to about 1 cm, such as from about 0.3 cm to about 0.9 cm, or from about 0.5 cm to about 0.7 cm, or from about 0.6 cm to about 1 cm.

The handle component 100 may include engagement elements complementary to engagement elements of the medical device 200 that permit selective attachment and detachment of the handle component 100 to the device 200. For example, the handle component 100 may include a ridge or groove having a size and shape complementary to a respective groove or ridge of the medical device. In the examples illustrated, the handle component 100 includes a ridge 120 on its outer surface proximate the distal end 102 of the body 110, and the medical device 200 includes a groove 222 on its inner surface proximate a proximal end 204 of the device 200. Thus, the handle component 100 may be coupled to the device 200 by inserting the distal end 102 of the body 110 into the device 200 such that the ridge 120 engages the groove 222.

Further details of the medical device 200 (e.g., baffle device) are shown in FIGS. 2A and 2B. The device 200 includes a body 210 that extends from the proximal end 204 to a distal end 202. The distal end 202 may be flexible and have a flared shape to facilitate contact with the convex curvature of the eye for topical administration of a composition, e.g., therapeutic ophthalmic composition, to the eye. The body 210 defines a lumen 250 that may receive a composition, e.g., formulated as a liquid or a gel, for contact with the eye.

An intermediate portion of the body 210 includes a bellows 212 able to expand and contract, depending on forces applied to the device 200. In particular, the bellows 212 extends radially outward in a symmetrical fashion, providing an internal space between proximal and distal ends of the bellows. Thus, the proximal and distal ends may move towards each other when a portion of the bellows 212 is compressed (decreasing the internal space of that compressed portion), and may move away from each other when a portion of the bellows 212 is expanded (increasing the internal space of that expanded portion). The bellows 212 may be flexible to permit compression and expansion of different portions of the bellows 112 (see, e.g., FIGS. 5A and 5B). The bellows 212 may be an equal distance between the proximal end 204 and the distal end 202, or may be closer to either the proximal end 204 or the distal end 202. In the example shown in the figures, the bellows 212 is somewhat closer to the distal end 202.

The bellows 212 may extend outward from the body 210 to form a general V-shape. While in a neutral position, the inner walls of the bellows 212 (defining a portion of the lumen 250) may have an angle ranging from about 45 degrees to about 75 degrees, such as about 50 degrees to about 70 degrees, or about 60 degrees to about 65 degrees. Thus, the bellows 212 may be capable of compression and expansion relative to the neutral position to decrease or increase, respectively, the inner angle of the bellows 212. Further, different portions of the bellows 212 may be compressed or expanded at the same time, discussed further below in connection to FIGS. 5A and 5B. In some aspects, the maximum width of the device 200 is defined by the bellows 212 or the distal end 202, or defined by both if the bellows 212 and the distal end 202 have the same width.

The wall thickness and flexibility of the body 210 of the device 200 may permit compression and expansion of the bellows 212 as the device 200 contacts the surface of the eye during administration of a therapeutic composition. The device 200 may have any of the wall thickness, length, and/or cross-sectional dimensions described above in connection to handle component 100. For example, the wall thickness of the body 210 may be less than 0.1 cm, e.g., ranging from about 0.01 cm to 0.1 cm, or from about 0.04 cm to about 0.09 cm. The total length of the device 200 from proximal end 204 to distal end 202 may range from about 1 cm to about 3 cm, such as about 1.5 cm to about 2.5 cm. The cross-sectional dimension (e.g., diameter) of the lumen 250 may range from about 0.2 cm to about 1 cm, such as from about 0.3 cm to about 0.9 cm, or from about 0.5 cm to about 0.7 cm, or from about 0.6 cm to about 1 cm. Additionally or alternatively, the width of the bellows 212 may range from about 1 cm to about 3 cm, such as about 1.5 cm to about 2.5 cm, from about 1.5 cm to about 2.0 cm. As mentioned above, in some cases, the maximum width of the device 200 is defined by the bellows 212.

FIG. 3 shows an example of the medical device 200 coupled to the handle component 100, e.g., via complementary engagement elements (ridge 120 and groove 222 as discussed above) proximate the distal end 102 of the handle component 100 and proximate the proximal end 204 of the medical device 200. When coupled with the handle component 100, the medical device 200 may provide a handle 105 for a user to position the distal end 202 of the device 200 over the eye of a patient during administration of a composition. The respective lumens 150, 250 may be aligned such that the composition may be introduced via the proximal end 104 of the handle component 100 through the handle component 100 and into the medical device 200 to contact the eye. The composition may remain in contact with the eye and enclosed within the body 210 of the medical device 200 as the distal end 202 forms a gentle seal against the eye. The user may maintain contact between the device 200 and the eye for a sufficient amount of time for active agents in the composition to enter inner tissues of the eye for therapeutic effect. The total length of the combined handle component 100 and medical device 200 when coupled together (from proximal end 104 to distal end 202) may range from about 1.8 cm to about 5.5 cm, such as from about 2 cm to about 5 cm, or from about 2.5 cm to about 4 cm.

As mentioned above, the medical device 200 need not be used in combination with a handle 105 or handle component 100. In some examples, a medical professional or other user may grasp the body 210 of the device 200 and gently place the distal end 202 of the device 200 against the eye. While holding the body 210, the user may introduce a composition into the lumen 250 via the open proximal end 204, such that the composition contacts the eye and enclosed within the body 210 for a sufficient amount of time to deliver active agent(s) of the composition to the eye.

According to additional aspects of the present disclosure, the device 200 may be coupled to a cartridge 400 and used in conjunction with a delivery device 300 as shown in FIG. 4 to administer a composition to the eye of a subject. Further discussion of delivery devices and cartridges thereof that may be used with the medical devices (baffle devices) herein are discussed in WO 2024/118773, incorporated by reference. The delivery device 300 includes a body 372 with a housing that includes a handle and an actuator 375, e.g., trigger, button, switch, etc. The body 372 defines a lumen or slot 378 that receives the cartridge 400. For example, the cartridge 400 may be insertable into the body 372 of the delivery device 300 for treatment of a subject, the cartridge 400 being single-use and removable from the delivery device 300 after treatment. For example, the cartridge 400 may include at least one tab 403 receivable within corresponding recesses 379 of the body 372. The cartridge 400 may be pre-loaded with the desired amount of active agent(s) for targeted delivery to the eye. For example, the cartridge may be preloaded with the composition or with reagents to be mixed together to prepare the composition shortly before administration to a subject as discussed in WO 2024/118773. Optionally, the cartridge 400 may include two or more subcartridges, the contents of which are mixed together shortly before administration to a subject. Such cartridges 400 may be useful for delivery of pH-sensitive compositions.

The end of the cartridge 400 opposite the tab(s) 403 may include engagement elements complementary to engagement elements of the medical device 200. For example, the cartridge 400 may include a ridge 420 (similar to the ridge 120 of handle component 100) with a size and shape complementary to the groove 222 of the device 200. Alternatively, the cartridge 400 may include a groove complementary to a ridge of the device 200. Thus, a user may insert the cartridge 400 preloaded with active agent(s) into the delivery device 300, and then attach the medical device 200 to the cartridge 400. The delivery device 300 may be operated as discussed in WO 2024/118773 to prepare the composition within the cartridge, and once the distal end 202 of the device 200 is gently placed against the subject's eye, to expel the composition from the cartridge 400 through the device 200 to contact and remain in contact with the eye for a suitable amount of time.

According to some aspects, the composition administered to the eye does not include a preservative. For example, the cartridge 400 may be sealed from environmental contamination prior to use and configured for single use with the desired amount of agent(s) in a single step administration to one eye. Thus, a separate cartridge 400 may be used to treat the other eye, e.g., in conjunction with a new, unused medical device 200 or after sterilizing the medical device 200 used to treat the first eye.

The present disclosure includes methods of delivering active agents, e.g., pharmaceutical agents and therapeutic agents, via topical administration to the eye. For example, the active agent(s) may treat the retina and/or other posterior structures by direct application via scleral tissues and/or the cornea. According to some aspects, the active agent(s)

administrated may comprise or be a retinal drug. Active agents delivered through the sclera may remain in suspension in the vitreous humor for a sufficient period of time for natural fluid activity for the active agents to come in contact with, and adhere to, the retina and other posterior structures of the eye. The quantity of active agent(s) delivered may achieve a desired pharmacological or therapeutic dose. Various active agents including retinal drugs may be administered to the eye, e.g., in a buffer solution. Exemplary active agents include, but are not limited to, bevacizumab, ranibizumab, ceftazidime, dexamethasone, aflibercept, fluocinolone, avacincaptad pegol, ocriplasmin, methotrexate, pegcetacoplan, triamcinolone, farcimab, and vancomycin. Exemplary buffer solutions include phosphate buffer, e.g., monobasic sodium phosphate, disodium hydrogen phosphate and/or potassium dihydrogen phosphate, and other alkaline pH buffer solutions such as a carbonate buffer. The buffer may have a pH ranging from about 7.5 to about 9.5, e.g., about 8.0 to about 9.0, or about 8.2 to about 8.5.

In some aspects, the composition also may comprise an acylating agent, e.g., useful for opening tight junctures of tissues of the eye. Acylating agents useful for the present disclosure include anhydrides, acid chlorides, sulfonyl chlorides, and sulfonic acid. Suitable anhydrides include agents that change the net charge from positive to negative. Exemplary anhydrides suitable for the devices and methods herein include, but are not limited to, maleic anhydride, succinic anhydride, glutaric anhydride, citractonic anhydride, methyl succinic anhydride, itaconic anhydride, methyl glutaric anhydride, dimethyl glutaric anhydride, phthalic anhydride, acetic anhydride, chloroacetic anhydride, propionic anhydride, butyric anhydride, isobutyric anhydride, isovaleric anhydride, and hexanoic anhydride. Anhydrides are sensitive to conversion to the corresponding acid (e.g., conversion of glutaric anhydride to glutaric acid) when exposed to and/or mixed with an aqueous solution. Such anhydrides are also reactive with deprotonated amines on protein molecules. Amine groups on protein molecules can be deprotonated by exposure to an alkaline buffer, for example. Exemplary acid chlorides suitable for the devices and methods herein include, but are not limited to, oxalyl chloride, malonyl chloride, acetyl chloride, propionyl chloride, dichloropropionyl chloride, butyryl chloride, isobutyryl chloride, and valeryl chloride. Exemplary sulfonyl chlorides suitable for the devices and methods herein include, but are not limited to, chlorosulfonylacetyl chloride, chlorosulfonylbenzoic acid, 4-chloro-3-(chlorosulfonyl)-5-nitroebnzoic acid, 3-(chlorosulfonyl)-P-anisic acid, ethane sulfonyl chloride, methane sulfonyl chloride, and 1-butane sulfonyl chloride. The active agent(s) and acylating agent may be administered sequentially, e.g., administration of the acylating agent followed by the active agent(s), or may be administered at the same time. For example, a composition comprising an active agent such as a retinal drug may be administered to the sclera of the eye.

The composition may be administered while the eye of the subject looks upward in a superior direction, that is, towards the top of the subject's head. This may increase the surface area of the sclera available for topical delivery of the composition. The methods herein may include a single administration of the composition to the eye, or may be repeated one or more times per eye. Optionally, a topical anesthetic may be applied to the eye before the composition is administered to the eye.

As mentioned above, the medical devices (baffle devices) herein facilitate topical administration of compositions to the eyes of different subjects in a bespoke manner. In particular, the flexibility of the bellows allows the device to accommodate different surface curvatures and/or to be positioned over different portions of an eye, depending on the tissues to be targeted and the type(s) of active agents to be delivered. Because the curvature of the eye typically is not uniform, the bellows allows the device to maintain contact with the eye during treatment.

Figure 5A:
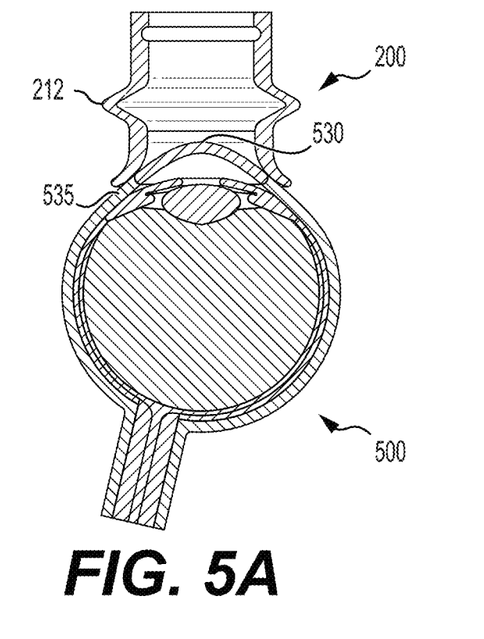
FIGS. 5A-5B show the medical device of FIGS. 2A-2B in different positions against the surface of an eye.
Figure 5B:
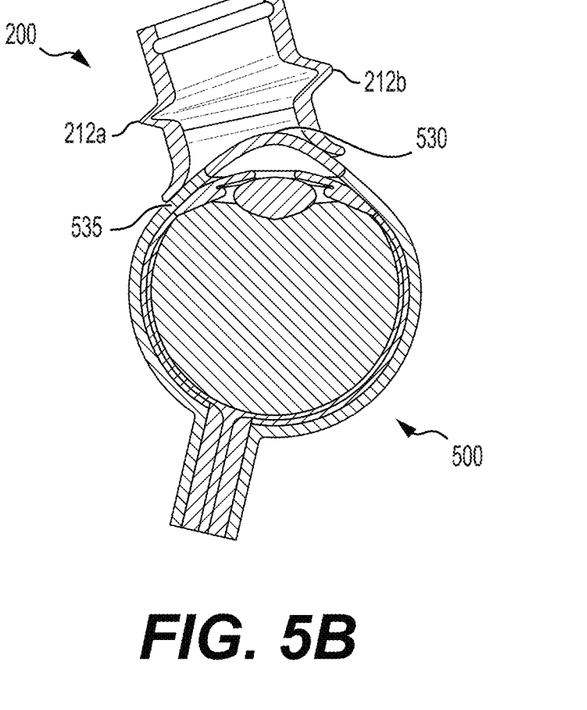

FIGS. 5A and 5B illustrate placement of the medical device 200 on the surface of an eye 500 of a subject (e.g., patient) as part of a medical procedure. FIGS. 5A and 5B show the device 200 in different positions, showing compression or expansion of the bellows 212 given the convex curvature of the eye 500. For example, FIG. 5A shows the device 200 centered on the cornea 530 of the eye 500. For example, a central longitudinal axis of the lumen 250 may coincide with a center of the cornea 530. When the surface of the eye 500 has a generally uniform and symmetric shape, the device 200 may be in a substantially neutral position while the distal end 202 of the device 200 contacts the surface of the eye 500. The device 200 may form a seal with the surface of the eye 500, such that a therapeutic composition is contained within an enclosed space provided between the walls of the device 200 and the surface of the eye 500. The surface of the eye 500 within the enclosed space may be an entirety of the cornea 530 and portions of the sclera 535 around the cornea 530. The composition may be introduced into the lumen 250 via the open proximal end 204 of the device 200, via the open proximal end 104 of a handle component 100 if the device 200 is used in conjunction with the handle component 100, or via a cartridge 400 if the composition is administered using a delivery device 300.

FIG. 5B illustrates the device 200 in a different, off-center position on the surface of the eye 500. In this position, the curvature of the surface of the eye 500 contacted by the distal end 202 of the device 200 varies, e.g., given the slightly bulging nature of the cornea 530. To accommodate this variation in curvature, the side 212a of the bellows 212 farthest from the cornea 530 is partially compressed while the opposite side 212b closer to the cornea 530 is either maintained in the neutral position or partially expanded. This relative compression and expansion afforded by the bellows 212 allows the distal end 202 of the device 200 to maintain contact with the surface of the eye 500. Accordingly, when a therapeutic composition is administered, the composition may be retained with the enclosed space provided between the walls of the device 200, despite the variation in shape of the eye 500.

For administration to a subject, a therapeutic composition may be delivered to the lumen of the baffle device in any appropriate manner. For example, the composition in liquid or gel form may be introduced to the device via a dropper or poured from a container while the device is positioned against the surface of the eye. The composition may be maintained in contact with the eye for a suitable amount of time to provide for delivery of active agent(s) of the composition to interior structures of the eye (e.g., endothelium, vitreous humor, retina, etc.). Depending on the active agent (s), the composition may be in contact with the eye for at least at least 15 seconds or at least 30 seconds, for example from about one minute to about two minutes. This amount of time may be sufficient for delivery of the active agent(s) to the targeted tissues.

It is intended that the specification and examples be considered as exemplary only, with a true scope and spirit of the present disclosure being indicated by the following claims.

The invention claimed is:

1. A medical device comprising:
   a body defining a lumen that extends from a proximal end of the body to a distal end of the body, wherein the body includes an intermediate portion that includes a compressible bellows, inner walls of the bellows defining a portion of the lumen;
   wherein the distal end of the body is flared, the distal end being configured to contact a convex surface of an eye; and
   wherein the distal end of the body is configured to maintain contact with the surface of the eye in a first position centered on a cornea of the eye and in a second position off-center from the cornea by compression and expansion of different portions of the bellows.

2. The device of claim 1, wherein the device further comprises a handle configured to be gripped by a user, the handle being integral with or coupled to the body.

3. The device of claim 1, wherein the device comprises a biocompatible polymer, and wherein the lumen has a diameter ranging from about 0.2 cm to about 1 cm at the proximal end of the body.

4. The device of claim 1, wherein a wall thickness of the bellows ranges from about 0.01 cm to about 0.1 cm.

5. The device of claim 1, wherein an inner angle of the bellows ranges from about 45 degrees to about 75 degrees.

6. The device of claim 1, wherein a maximum width of the device is defined by the bellows, the distal end, or both the bellows and the distal end.

7. The device of claim 1, wherein the bellows is closer to the distal end than to the proximal end.

8. A method of treating an eye of a subject, the method comprising:
   placing a distal end of a body of a medical device against a surface of the eye, wherein the body defines a lumen that extends from a proximal end of the body to a distal end of the body, wherein the body comprises an intermediate portion that includes a compressible bellows with inner walls that define a portion of the lumen;
   adjusting a position of the body relative to the surface of the eye while the distal end of the body forms a seal against the surface of the eye, wherein adjusting the position includes compression and expansion of different portions of the bellows; and
   introducing a therapeutic composition to the lumen through the proximal end of the body to contact the surface of the eye.

9. The method of claim 8, wherein the distal end of the body flares radially outward.

10. The method of claim 8, wherein adjusting the position of the body includes compressing a first portion of the bellows while a remainder of the bellows is uncompressed or expanded.

11. The method of claim 10, wherein an inner angle of the bellows in a neutral position ranges from about 45 degrees to about 75 degrees, and wherein the portion of the bellows is compressed relative to the neutral position.

12. The method of claim 8, wherein a wall thickness of the bellows ranges from about 0.01 cm to about 0.1 cm.

13. The method of claim 8, wherein the therapeutic composition comprises one or more active agents and a buffer solution.

14. The method of claim 8, wherein the composition contacts the surface of the eye for about 30 seconds to about two minutes.

15. The method of claim 8, wherein the subject has keratoconus or astigmatism.

16. The method of claim 8, wherein the device is centered on a cornea of the eye when the composition contacts the surface of the eye.

17. The method of claim 8, wherein the device is off-center relative to a cornea of the eye when the composition contacts the surface of the eye.

18. A medical device comprising:
   a body defining a lumen that extends from a proximal end of the body to a distal end of the body, wherein the body includes an intermediate portion that includes a compressible bellows, wherein inner walls of the bellows defining a portion of the lumen, a wall thickness of the bellows ranges from about 0.01 cm to about 0.1 cm, and an inner angle of the bellows ranges from about 45 degrees to about 75 degrees;
   wherein the distal end of the body is flared, the distal end being configured to contact a convex surface of an eye; and
   wherein the distal end of the body is configured to maintain contact with the surface of the eye in a first position centered on a cornea of the eye and in a second position off-center from the cornea by compression and expansion of different portions of the bellows.

19. The medical device of claim 18, wherein the bellows is closer to the distal end than to the proximal end.

20. The medical device of claim 18, wherein a length of the body of the device from the proximal end to the distal end ranges from about 1 cm to about 5.5 cm.

* * * * *